United States Patent [19]

Inoue et al.

[11] 4,390,736
[45] Jun. 28, 1983

[54] PROCESS FOR PRODUCING PHENOLS

[75] Inventors: Yasuhiko Inoue, Niihama; Shigeo Wake, Saijo; Tamio Sirafuji, Chiba; Masazo Beppu, Niihama, all of Japan

[73] Assignee: Sumitomo Chemical Company, Limited, Osaka, Japan

[21] Appl. No.: 320,106

[22] Filed: Nov. 10, 1981

[30] Foreign Application Priority Data

Nov. 26, 1980 [JP] Japan ................................ 55-167083
Feb. 27, 1981 [JP] Japan ................................ 56-29149
Aug. 21, 1981 [JP] Japan ................................ 56-131693

[51] Int. Cl.³ ............................................. C07C 37/01
[52] U.S. Cl. .................................... 568/801; 568/802
[58] Field of Search ................................ 568/801, 802

[56] References Cited

U.S. PATENT DOCUMENTS

| Re. 24,848 | 7/1960 | Kaeding et al. | 568/801 |
| 2,727,926 | 12/1955 | Kaeding | 568/801 |
| 2,852,567 | 9/1958 | Barnard et al. | 568/801 |
| 3,277,184 | 10/1966 | Ryland et al. | 568/801 |

FOREIGN PATENT DOCUMENTS

| 719287 | 10/1965 | Canada | 568/801 |
| 39-25115 | 11/1964 | Japan | 568/802 |
| 40-5686 | 3/1965 | Japan | 568/802 |
| 54-72789 | 6/1979 | Japan | 568/802 |
| 978918 | 1/1965 | United Kingdom | 568/801 |

Primary Examiner—Werren B. Lone
Attorney, Agent, or Firm—Stevens, Davis, Miller & Mosher

[57] ABSTRACT

A method for production of phenol or nucleus-substituted phenols from benzoic acid or nucleus-substituted benzoic acids by gas-phase catalytic oxidation characterized by using an oxide catalyst of the formula, $$Mo_aW_bX_cY_dZ_eO_f$$

wherein Mo is molybdenum, W is at least one of vanadium, niobium and tantalum, X is at least one of copper, silver, manganese, iron, cobalt, nickel, rhodium, palladium and platinum, Y is at least one of cerium, uranium, zirconium, chromium, tungsten, zinc, cadmium, tin, phosphorus, antimony, bismuth and tellurium, Z is at least one of thallium, alkali metals and alkaline earth metals, and when a is fixed to 12, b is 0.1 to 60, c is 0.1 to 60, d is 0 to 24, e is 0.1 to 120 and f is the number of oxygen atoms satisfying the valence of other elements.

7 Claims, No Drawings

PROCESS FOR PRODUCING PHENOLS

The present invention relates to a method for the production of phenol or nucleus-substituted phenols by gas-phase catalytic oxidation of benzoic acid or nucleus-substituted benzoic acids.

It is well known that copper compounds are used as catalysts for producing phenol or nucleus-substituted phenols from benzoic acid or nucleus-substituted benzoic acids. For example, U.S. Pat. No. 2,727,926 (U.S. Pat. No. Re. 24848) discloses a method for the production of phenol by oxidation of aromatic mono-carboxylic acids in liquid phase with a molecular oxygen-containing gas in the presence of a copper compound. But his liquid-phase process has many problems in terms of tar formation, and loss of the catalyst, useful substances being caught in the tar as well as catalyst recovery. U.S. Pat. No. 2,852,567, Japanese Patent Publication Nos. 25115/1964 and 5686/1965 and Japanese Patent Publication Kokai (Laid-Open) No. 72789/1979 disclose a method for the production of phenol compounds by gas-phase catalytic oxidation of aromatic carboxylic acids with catalysts containing a copper compound. But, U.S. Pat. No. 2,852,567 gives a phenol selectivity of only about 20 to about 65%. The patent publication No. 25115/1964 gives a conversion of benzoic acid as low as 5.5 to 9.6%, and produces large amounts of phenyl benzoate in addition to phenol, requiring a hydrolysis step later. The patent publication No. 5686/1965 uses catalysts containing one or more of alkali metals and/or alkaline earth metals and one or more of didymium, zirconium, molybdenum and vanadium in addition to the copper compound, but catalysts of Cu-Mo and Cu-V types are low in both the conversion of benzoic acid and the selectivity of phenol. Also, the patent publication Kokai (Laid-Open) No. 72789/1979 gives a phenol selectivity of 70 to 80 mole % in the examples, but it requires large quantities of steam as shown by a molar ratio of steam: benzoic acid of 33-74, causing a problem that a steam unit, quantity of steam required for the production of a unit weight of product, becomes very high.

Further, when an exothermic reaction like the reaction of the present invention is carried out with these catalysts mainly composed of a copper compound, a problem of reaction control arises because a copper catalyst easily forms hot spots and, on being exposed to high temperature, undergoes sintering to which lowers catalytic activity.

The inventors extensively studied to improve these prior-art methods, and found that, in the production of phenol or nucleus-substituted phenols by gas-phase catalytic oxidation of benzoic acid or nucleus-substituted benzoic acids, phenol or nucleus-substituted phenols are obtained in a high selectivity using a specified oxide catalyst. The inventors thus attained the present invention.

In the method for the production of phenol or nucleus-substituted phenols of the formulae (II),

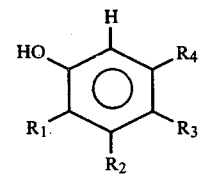

wherein $R_1$, $R_2$, $R_3$ and $R_4$ are each a hydrogen atom or a methyl group, and/or (III),

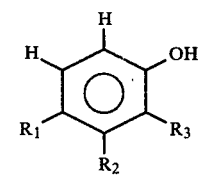

wherein $R_1$, $R_2$ and $R_3$ are as defined above, by gas-phase catalytic oxidation of benzoic acid or nucleus-substituted benzoic acids of the formula (I),

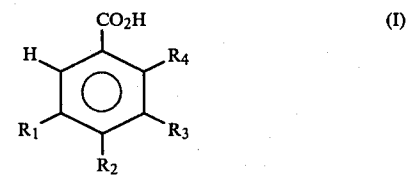

wherein $R_1$, $R_2$, $R_3$ and $R_4$ are as defined above, the present invention provides a method for the production of phenol or nucleus-substituted phenols comprising using an oxide catalyst of the formula, $$Mo_aW_bX_cY_dZ_eO_f$$

wherein Mo is molybdenum, W is at least one of vanadium, niobium and tantalum, X is at least one of copper, silver, manganese, iron, cobalt, nickel, rhodium, palladium and platinum, Y is at least one of cerium, uranium, zirconium, chromium, tungsten, zinc, cadmium, tin, phosphorus, antimony, bismuth and tellurium, Z is at least one of thallium, alkali metals and alkaline earth metals, and when a is fixed to 12, b is 0.1 to 60, c is 0.1 to 60, d is 0 to 24, e is 0.1 to 120 and f is the number of oxygen atoms satisfying the valence of other elements.

The use of the catalyst of the present invention is very advantageous industrially in that: great improvements are observed in the conversion of benzoic acid or nucleus-substituted benzoic acids as well as the selectivity of phenol or nucleus-substituted phenols; diphenyl, diphenyl ether and phenyl benzoate as by-products are extremely decreased even if steam is supplied in lower quantities as compared with the conventional catalysts; the thermal resistance of the catalyst is so good that hot spots are very difficult to form and the reaction is easily controllable; and catalytic activity develops at low temperatures, so that the reaction temperature can be lowered.

Next, the present invention will be illustrated in detail.

As benzoic acids used as material in the present invention, there are given for example benzoic acid, 2-, 3- or 4-methylbenzoic acid, 2,3-, 2,4-, 2,5-, 3,5- or 3,5- dimethylbenzoic acid, 2,3,5-, 3,4,5- or 2,3,4-trimethylbenzoic acid and 2,3,4,5-tetramethylbenzoic acid.

The catalyst used in the present invention includes oxides comprising (a) molybdenum, (b) at least one of vanadium, niobium and tantalum, (c) at least one of copper, silver, manganese, iron, cobalt, nickel, rhodium, palladium and platinum, and (e) at least one of thallium, alkali metals and alkaline earth metals, or (a) molybdenum, (b) at least one of vanadium, niobium and tantalum, (c) at least one of copper, silver, manganese, iron, cobalt, nickel, rhodium, palladium and platinum, (d) at least one of cerium, uranium, zirconium, chromium, tungsten, zinc, cadmium, tin, phosphorus, antimony, bismuth and tellurium, and (e) at least one of thallium, alkali metals and alkaline earth metals.

The catalyst of the present invention provides good reaction results in its wide composition range, and particularly, it provides further good results when used as a catalyst of the following experimental formula, $$Mo_a W_b X_c Y_d Z_e O_f$$

wherein Mo is molybdenum, W is at least one of vanadium, niobium and tantalum, X is at least one of copper, silver, manganese, iron, cobalt, nickel, rhodiumm, palladium and platinum, Y is at least one of cerium, uranium, zirconium, chromium, tungsten, zinc, cadmium, tin, phosphorus, antimony, bismuth and tellurium, Z is at least one of thallium, alkali metals and alkaline earth metals, and when a is fixed to 12, b is 0.1 to 60, preferably 1 to 24, c is 0.1 to 60, preferably 1 to 40, d is 0 to 24, preferably 0 to 12, more preferably 0.1 to 12, e is 0.1 to 120, preferably 12 to 90, and f is the number of oxygen atoms satisfying the valences of other elements.

In producing the catalyst used in the present invention, methods for preparing this type of oxide catalyst are generally employed. For example, of the materials constituting the catalyst, as molybdenum compounds are used ammonium molybdate, molybdic acid, molybdenum oxide and etc.; as vanadium compounds are used ammonium metavanadate, vanadium pentoxide, vanadyl oxalate, vanadyl sulfate and etc.; and as compounds of niobium, tantalum, copper, silver, manganese, iron, cobalt, nickel, rhodium, palladium, platinum, cerium, uranium, zirconium, chromium, tungsten, zinc, cadmium, tin, phosphorus, antimony, bismuth, tellurium, thallium, alkali metals and alkaline earth metals; nitrates, carbonates, organic acid salts, halides, hydroxides, oxides and etc. of these metals are effectively used.

These compounds as material are made into a solution or slurry with solvents such as water, and after mixing as uniformly as possible, the solvent is evaporated to dryness on a sand bath. The cake obtained is dried, calcined at 500° to 850° C., preferably 600° to 800° C., and then pulverized. When this calcining temperature is lower than 500° C., catalysts obtained lower the selectivity of phenols. When the temperature is more than 850° C., there is observed a tendency to lower the conversion of benzoic acids. The pulverized cake obtained above is calcined, after formed into tablets or as it is, at 300° to 700° C. to obtain the catalyst.

The catalyst of the present invention is very effective, if not supported on carriers, but supporting it on carriers is more favorable. The carriers include for example silica gel, silica sol, alumina, silica-alumina, silicon carbide, diatomaceous earth and titanium oxide. The form of catalyst includes for example extrusion forms, pellets, coating forms and impregnation forms.

In the present invention, oxygen is supplied to the reaction system together with benzoic acids as material, and its amount is 0.25 to 10 times by mole, preferably 0.5 to 5 times by mole based on benzoic acids. When the amount exceeds this range, complete oxidation of benzoic acids occurs easily. When the amount is too far below this range, the conversion of benzoic acids becomes too low. As to the form of oxygen, any of pure oxygen and inert gas-diluted oxygen will do.

In the present invention, steam is supplied to the reaction system together with benzoic acids, and its amount is 0.5 to 40 times by mole, preferably 1 to 30 times by mole, based on benzoic acids. To markedly exceed this range is not economical. While amounts too far below this range increase the amount of by-products such as diphenyl, diphenyl ether, carbon dioxide gas and etc., thereby lowering the selectivity of phenols. Also, since steam acts to hydrolyze phenyl benzoate, which is an intermediate, amounts too far below this range make the hydrolysis of phenyl benzoate difficult to occur, as a result of which the selectivity of phenols is lower and hydrolysis becomes necessary after the gas-phase catalytic oxidation.

The reaction temperature is 200° to 600° C., preferably 250° to 400° C. When the temperature is too high above this range, side reactions such as complete oxidation and decarboxylation of benzoic acids occur to lower the selectivity of phenols. When the temperature is too far below this range, the rate of reaction becomes slow making the process uneconomical.

The reaction pressure is not particularly limited, so far as the reaction system keeps a gaseous state under the reaction conditions, but generally atmospheric pressure or higher is preferred.

The space velocity of reaction gas is 100 to 10000 $hr^{-1}$, preferably 500 to 5000 $hr^{-1}$, but it may be selected optionally depending upon the composition of reaction gas, type of catalyst, and reaction temperature.

The reaction of the present invention may be achieved by using any of fixed bed, moving bed and fluidized bed.

As described above, the method of the present invention enables phenol or nucleus-substituted phenols to be obtained with high selectivity, and therefore, it is very useful industrially.

The present invention will be illustrated in more detail with reference to the following examples, which are not however to be interpreted as limiting the invention thereto. Unless otherwise stated, all percents in the examples are by mole.

EXAMPLE 1

3.47 Grams of ammonium molybdate (Mo, 19.6 m-atom), 1.17 g of ammonium metavanadate (V, 10.0 m-atom) and 2.37 g of copper nitrate (Cu, 9.8 m-atom) were dissolved in a mixture of 75 g of 28% aqueous ammonia, 4 g of monoethanolamine and 80 g of ion-exchanged water, and 30 g of 10 to 16-mesh γ-alumina (KHA-24 produced by Sumitomo Aluminum Smelting Co.) was added thereto. After heating at 80° C. for 10 minutes, the liquor was evaporated to dryness in an evaporator under reduced pressure over 1 hour, followed by calcining at 750° C. for 2 hours.

This product was added to 20 g of ion-exchanged water containing 0.78 g of sodium hydroxide (Na, 19.6 m-atom), and the liquor was evaporated to dryness in an evaporator, followed by calcining again at 600° C. for 8 hours. The catalyst thus obtained had a composition of $Mo_{12}V_{6.1}Cu_6Na_{12}O_{63.25}$, as expressed in atomic ratio.

Five milliliters of this catalyst was packed in a glass reaction tube, 10 mm in inside diameter and 300 mm in length, at the middle part thereof, and silicon carbide was packed as pre-heating zone above the catalyst. The reaction tube was heated to 300° C., and reaction was carried out by supplying 1.22 g (10.0 mmole)/hr of benzoic acid, 3.3 g (183 mmole)/hr of water, 0.224 l (10 mmole)/hr of oxygen and 2.016 l (90 mmole)/hr of nitrogen.

The mixed gas from the reaction tube was cooled and liquefied by means of a cooler and analyzed gas-chromatographically and chemically.

As a result, it was found that the conversion of benzoic acid was 65%, and the selectivity of phenol, phenyl benzoate, benzene, and diphenyl+diphenyl ether was 88%, negligibly small, 2% and 6%, respectively.

obtained had a composition of $V_{12}Cu_6Na_{12}O_{42}$ as expressed in atomic ratio.

Analysis of the reaction gas showed that the conversion of benzoic acid was 35.8%, and the selectivity of phenol, phenyl benzoate, benzene, and diphenyl+diphenyl ether was 61.6%, negligibly small, 5% and 6%, respectively.

EXAMPLES 2 TO 7

Procedure was carried out in the same manner as in Example 1 except that sodium hydroxide was replaced by each of 0.82 g of lithium hydroxide (Li, 19.6 m-atom), 5.0 g of magnesium nitrate (Mg, 19.6 m-atom), 5.22 g of thallium nitrate (Tl, 19.6 m-atom), 5.56 g of strontium nitrate (Sr, 19.6 m-atom), 1.10 g of potassium hydroxide (K, 19.6 m-atom) and 3.22 g of calcium nitrate (Ca, 19.6 m-atom). The results are shown in Table 1.

TABLE 1

| Example | Composition of catalyst | Reaction temperature (°C.) | Conversion of benzoic acid (%) | Selectivity (%) | | | |
|---|---|---|---|---|---|---|---|
| | | | | Phenol | Phenyl benzoate | Benzene | Diphenyl + diphenyl ether |
| 2 | $Mo_{12}V_{6.1}Cu_6Li_{12}O_{63.25}$ | 300 | 55 | 82 | 1 | 3 | 2 |
| 3 | $Mo_{12}V_{6.1}Cu_6Mg_{12}O_{69.25}$ | 300 | 47 | 86 | 1 | 2 | 1 |
| 4 | $Mo_{12}V_{6.1}Cu_6Tl_{12}O_{63.25}$ | 300 | 46 | 84 | 1 | 2 | 4 |
| 5 | $Mo_{12}V_{6.1}Cu_6Sr_{12}O_{69.25}$ | 300 | 45 | 82 | Trace | 1 | 3 |
| 6 | $Mo_{12}V_{6.1}Cu_6K_{12}O_{63.25}$ | 300 | 55 | 80 | 1 | 5 | 5 |
| 7 | $Mo_{12}V_{6.1}Cu_6Ca_{12}O_{69.25}$ | 300 | 40 | 81 | Trace | 1 | 1 |

COMPARATIVE EXAMPLE 1

Procedure was carried out in the same manner as in Example 1 except that 1.17 g of ammonium metavanadate (V, 19.6 m-atom) was not added and the reaction was carried out at 340° C. The catalyst thus obtained had a composition of $Mo_{12}Cu_6Na_{12}O_{48}$ as expressed in atomic ratio.

Analysis of the reaction gas showed that the conversion of benzoic acid was 37.6%, and the selectivity of phenol, phenyl benzoate, benzene, and diphenyl+diphenyl ether was 63.5%, negligibly small, 4% and 6%, respectively.

EXAMPLES 8 TO 15

Catalyst preparation and reaction were carried out in the same manner as in Example 1 except that copper nitrate was replaced by each of 5.08 g of chloroplatinic acid (Pt, 9.8 m-atom), 2.46 g of manganese nitrate (Mn, 9.8 m-atom), 3.96 g of iron nitrate (Fe, 9.8 m-atom), 2.85 g of cobalt nitrate (Co, 9.8 m-atom), 2.85 g of nickel nitrate (Ni, 9.8 m-atom), 1.66 g of silver nitrate (Ag, 9.8 m-atom), 1.74 g of palladium chloride (Pd, 9.8 m-atom) and 2.58 g of rhodium chloride (Rh, 9.8 m-atom). The results are shown in Table 2.

TABLE 2

| Example | Composition of catalyst | Reaction temperature (°C.) | Conversion of benzoic acid (%) | Selectivity (%) | | | |
|---|---|---|---|---|---|---|---|
| | | | | Phenol | Phenyl benzoate | Benzene | Diphenyl + diphenyl ether |
| 8 | $Mo_{12}V_{6.1}Pt_6Na_{12}O_{69.25}$ | 300 | 65 | 80 | Trace | 5 | 2 |
| 9 | $Mo_{12}V_{6.1}Mn_6Na_{12}O_{66.25}$ | 300 | 43 | 75 | Trace | 1 | 1 |
| 10 | $Mo_{12}V_{6.1}Fe_6Na_{12}O_{66.25}$ | 300 | 50 | 78 | 1 | 1 | 5 |
| 11 | $Mo_{12}V_{6.1}Co_6Na_{12}O_{66.25}$ | 300 | 45 | 79 | 1 | 1 | 2 |
| 12 | $Mo_{12}V_{6.1}Ni_6Na_{12}O_{63.25}$ | 300 | 42 | 75 | 1 | 1 | 1 |
| 13 | $Mo_{12}V_{6.1}Ag_6Na_{12}O_{60.25}$ | 300 | 55 | 82 | 1 | 1 | 1 |
| 14 | $Mo_{12}V_{6.1}Pd_6Na_{12}O_{63.25}$ | 300 | 60 | 80 | Trace | 1 | 1 |
| 15 | $Mo_{12}V_{6.1}Rh_6Na_{12}O_{66.25}$ | 300 | 50 | 79 | 1 | 1 | 2 |

6%, respectively.

COMPARATIVE EXAMPLE 2

Procedure was carried out in the same manner as in Example 1 except that 2.29 g of ammonium metavanadate (V, 19.6 m-atom) was used in place of 3.47 g of ammonium molybdate (Mo, 19.6 m-atom) and 1.17 g of ammonium metavanadata (V, 10 m-atom), and that the reaction was carried out at 340° C. The catalyst thus

EXAMPLES 16 AND 17

Catalyst preparation and reaction were carried out in the same manner as in Example 1 except that ammonium metavanadate was replaced by each of 1.33 g of niobium pentoxide (Nb, 10.0 m-atom) and 2.21 g of tantalum pentoxide (Ta, 10.0 m-atom). The results are shown in Table 3.

TABLE 3

| Example | Composition of catalyst | Reaction temperature (°C.) | Conversion of benzoic acid (%) | Selectivity (%) | | | |
|---|---|---|---|---|---|---|---|
| | | | | Phenol | Phenyl benzoate | Benzene | Diphenyl + diphenyl ether |
| 16 | $Mo_{12}Nb_{6.1}Cu_6Na_{12}O_{63.25}$ | 300 | 50 | 80 | 1 | 5 | 7 |
| 17 | $Mo_{12}Ta_{6.1}Cu_6Na_{12}O_{63.25}$ | 300 | 50 | 80 | 1 | 6 | 8 |

EXAMPLE 18

1.73 Grams of ammonium molybdate (Mo, 9.8 m-atom), 1.72 g of ammonium metavanadate (V, 14.7 m-atom), 4.14 g of copper nitrate (Cu, 17.1 m-atom) and 0.29 g of zinc nitrate (Zn, 0.98 m-atom) were added to a mixture of 75 g of 28% aqueous ammonia, 4 g of monoethanolamine and 80 g of ion-exchanged water, and 30 g of 10 to 16-mesh γ-alumina (KHA-24 produced by Sumitomo Aluminum Smelting Co.) was added thereto. After heating at 80° C. for 10 minutes, the liquor was evaporated to dryness in an evaporator under reduced pressure over 1 hour, followed by calcining at 750° C. for 2 hours. This product was added to 20 g of ion-exchanged water containing 1.86 g of sodium hydroxide (Na, 46.6 m-atom), and the liquor was evaporated to dryness in an evaporator, followed by calcining again at 600° C. for 8 hours. The catalyst thus obtained had a composition of $Mo_{12}V_{18}Cu_{21}Zn_{1.2}Na_{57}O_{131.7}$, as expressed in atomic ratio.

Five milliliters of this catalyst was packed in a glass reaction tube, 10 mm in inside diameter and 300 mm in length, at the middle part thereof, and silicon carbide was packed as preheating zone above the catalyst. The reaction tube was heated to 300° C., and reaction was carried out by supplying 1.22 g (10.0 mmole)/hr of benzoic acid, 3.24 g (180 mmole)/hr of water, 0.224 l (10 mmole)/hr of oxygen and 2.016 l (90 mmole)/hr of nitrogen.

The mixed gas from the reaction tube was cooled and liquefied by means of a cooler and analyzed gas-chromatographically and chemically.

Carbon dioxide gas in the mixed gas was analyzed gas-chromatographically after cooling and liquefaction of the mixed gas.

As a result, it was found that the conversion of benzoic acid was 86%, and the selectivity of phenol, benzene, diphenyl+diphenyl ether and carbon dioxide gas was 91%, 1%, 5% and 3%, respectively.

EXAMPLES 19 TO 24

Catalyst preparation and reaction were carried out in the same manner as in Example 18 except that 1.86 g of sodium hydroxide (Na, 46.6 m-atom) was replaced by each of 1.95 g of lithium hydroxide (Li, 46.6 m-atom), 11.89 g of magnesium nitrate (Mg, 46.6 m-atom), 12.41 g of thallium nitrate (Tl, 46.6 m-atom), 13.22 g of strontium nitrate (Sr, 46.6 m-atom), 2.62 g of potassium hydroxide (K, 46.6 m-atom) and 7.66 g of calcium nitrate (Ca, 46.6 m-atom). The results are shown in Table 4.

TABLE 4

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 19 | $Mo_{12}V_{18}Cu_{21}Zn_{1.2}Li_{57}O_{131.7}$ | 300 | 65 | 90 | 0 | 2 | 8 |
| 20 | $Mo_{12}V_{18}Cu_{21}Zn_{1.2}Mg_{57}O_{160.2}$ | 300 | 55 | 90 | 2 | 3 | 5 |
| 21 | $Mo_{12}V_{18}Cu_{21}Zn_{1.2}Tl_{57}O_{131.7}$ | 300 | 52 | 91 | 1 | 4 | 4 |
| 22 | $Mo_{12}V_{18}Cu_{21}Zn_{1.2}Sr_{57}O_{160.2}$ | 300 | 50 | 89 | 1 | 5 | 5 |
| 23 | $Mo_{12}V_{18}Cu_{21}Zn_{1.2}K_{57}O_{131.7}$ | 300 | 80 | 90 | 4 | 4 | 2 |
| 24 | $Mo_{12}V_{18}Cu_{21}Zn_{1.2}Ca_{57}O_{160.2}$ | 300 | 55 | 89 | 1 | 4 | 6 |

EXAMPLES 25 TO 35

Catalyst preparation and reaction were carried out in the same manner as in Example 18 except that 0.29 g of zinc nitrate (Zn, 0.98 m-atom) was replaced by each of 0.547 g of cerous nitrate (Ce, 0.98 m-atom), 0.492 g of uranium nitrate (U, 0.98 m-atom), 0.262 g of zirconium oxynitrate (Zr, 0.98 m-atom), 0.392 g of chromium nitrate (Cr, 0.98 m-atom), 0.245 g of tungstic acid (W, 0.98 m-atom), 0.302 g of cadmium nitrate (Cd, 0.98 m-atom), 0.185 g of stannous chloride (Sn, 0.98 m-atom), 0.096 g of phosphoric acid (P, 0.98 m-atom), 0.143 g of antimony oxide (Sb, 0.98 m-atom), 0.228 g of bismuth oxide (Bi, 0.98 m-atom) and 0.225 g of telluric acid (Te, 0.98 m-atom). The results are shown in Table 5.

TABLE 5

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 25 | $Mo_{12}V_{18}Cu_{21}Ce_{1.2}Na_{57}O_{132.3}$ | 300 | 82 | 88 | 1 | 6 | 5 |
| 26 | $Mo_{12}V_{18}Cu_{21}U_{1.2}Na_{57}O_{134.1}$ | 300 | 80 | 87 | 1 | 5 | 7 |
| 27 | $Mo_{12}V_{18}Cu_{21}Zr_{1.2}Na_{57}O_{132.9}$ | 300 | 88 | 93 | Trace | 5 | 2 |
| 28 | $Mo_{12}V_{18}Cu_{21}Cr_{1.2}Na_{57}O_{134.1}$ | 300 | 89 | 88 | 1 | 5 | 6 |
| 29 | $Mo_{12}V_{18}Cu_{21}W_{1.2}Na_{57}O_{134.1}$ | 300 | 90 | 90 | Trace | 6 | 4 |
| 30 | $Mo_{12}V_{18}Cu_{21}Cd_{1.2}Na_{57}O_{131.7}$ | 300 | 80 | 85 | 1 | 8 | 6 |
| 31 | $Mo_{12}V_{18}Cu_{21}Sn_{1.2}Na_{57}O_{132.9}$ | 300 | 89 | 86 | 2 | 7 | 7 |
| 32 | $Mo_{12}V_{18}Cu_{21}P_{1.2}Na_{57}O_{133.5}$ | 300 | 85 | 91 | 1 | 4 | 4 |

TABLE 5-continued

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 33 | $Mo_{12}V_{18}Cu_{21}Sb_{1.2}Na_{57}O_{133.5}$ | 300 | 80 | 86 | 1 | 8 | 7 |
| 34 | $Mo_{12}V_{18}Cu_{21}Bi_{1.2}Na_{57}O_{132.3}$ | 300 | 80 | 87 | 1 | 6 | 6 |
| 35 | $Mo_{12}V_{18}Cu_{21}Te_{1.2}Na_{57}O_{132.9}$ | 300 | 89 | 92 | Trace | 5 | 3 |

EXAMPLES 36 TO 43

Catalyst preparation and reaction were carried out in the same manner as in Example 18 except that 4.14 g of copper nitrate (Cu, 17.1 m-atom) was replaced by each of 8.86 g of chloroplatinic acid (Pt, 17.1 m-atom), 4.29 g of manganese nitrate (Mn, 17.1 m-atom), 6.91 g of iron nitrate (Fe, 17.1 m-atom), 4.98 g of cobalt nitrate (Co, 17.1 m-atom), 4.98 g of nickel nitrate (Ni, 17.1 m-atom), 2.90 g of silver nitrate (Ag, 17.1 m-atom), 3.03 g of palladium chloride (Pd, 17.1 m-atom) and 4.50 g of rhodium chloride (Rh, 17.1 m-atom). The results are shown in Table 6.

EXAMPLES 46 TO 48

Catalyst preparation and reaction were carried out in the same manner as in Example 1 except that 3.47 g of ammonium molybdate (Mo, 19.6 m-atom) was replaced by 1.73 g of the ammonium molybdate (Mo, 9.8 m-atom); 1.17 g of ammonium metavanadate (V, 10.0 m-atom) was replaced by each of 0.095 g (V, 0.817 m-atom), 1.72 g (V, 14.7 m-atom) and 3.44 g (V, 29.4 m-atom) of the ammonium metavanadate; 2.37 g of copper nitrate (Cu, 9.8 m-atom) was replaced by 4.14 g of the copper nitrate (Cu, 17.1 m-atom); and 0.78 g of sodium hydroxide (Na, 19.6 m-atom) was replaced by 2.74 g of the sodium hydroxide (Na, 68.6 m-atom).

The results are shown in Table 8.

TABLE 6

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 36 | $Mo_{12}V_{18}Pt_{21}Zn_{1.2}Na_{57}O_{152.7}$ | 300 | 85 | 91 | 2 | 4 | 3 |
| 37 | $Mo_{12}V_{18}Mn_{21}Zn_{1.2}Na_{57}O_{163.2}$ | 300 | 63 | 85 | 1 | 3 | 11 |
| 38 | $Mo_{12}V_{18}Fe_{21}Zn_{1.2}Na_{57}O_{163.2}$ | 300 | 70 | 88 | 0 | 6 | 6 |
| 39 | $Mo_{12}V_{18}Co_{21}Zn_{1.2}Na_{57}O_{163.2}$ | 300 | 65 | 89 | 0 | 2 | 9 |
| 40 | $Mo_{12}V_{18}Ni_{21}Zn_{1.2}Na_{57}O_{131.7}$ | 300 | 62 | 87 | 1 | 2 | 10 |
| 41 | $Mo_{12}V_{18}Ag_{21}Zn_{1.2}Na_{57}O_{121.2}$ | 300 | 65 | 89 | 1 | 3 | 7 |
| 42 | $Mo_{12}V_{18}Pd_{21}Zn_{1.2}Na_{57}O_{131.7}$ | 300 | 70 | 90 | 1 | 4 | 5 |
| 43 | $Mo_{12}V_{18}Rh_{21}Zn_{1.2}Na_{57}O_{163.2}$ | 300 | 60 | 90 | 1 | 3 | 6 |

TABLE 8

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 46 | $Mo_{12}V_{1}Cu_{21}Na_{84}O_{101.5}$ | 300 | 67 | 80 | 6 | 9 | 5 |
| 47 | $Mo_{12}V_{18}Cu_{21}Na_{84}O_{144.0}$ | 300 | 75 | 89 | 1 | 7 | 3 |
| 48 | $Mo_{12}V_{36}Cu_{21}Na_{84}O_{189.0}$ | 300 | 70 | 81 | 2 | 7 | 10 |

EXAMPLES 44 AND 45

Catalyst preparation and reaction were carried out in the same manner as in Example 18 except that 1.72 g of ammonium metavanadate (V, 14.7 m-atom) was replaced by each of 1.95 g of niobium pentoxide (Nb, 14.7 m-atom) and 3.25 g of tantalum pentoxide (Ta, 14.7 m-atom). The results are shown in Table 7.

EXAMPLES 49 AND 50

Catalyst preparation and reaction were carried out in the same manner as in Example 47 except that 4.14 g of copper nitrate (Cu, 17.1 m-atom) was replaced by each of 0.197 g (Cu, 0.187 m-atom) and 7.10 g (Cu, 29.4 m-atom) of the copper nitrate.

The results are shown in Table 9.

TABLE 7

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 44 | $Mo_{12}Nb_{18}Cu_{21}Zn_{1.2}Na_{57}O_{131.7}$ | 300 | 65 | 90 | 2 | 5 | 3 |
| 45 | $Mo_{12}Ta_{18}Cu_{21}Zn_{1.2}Na_{57}O_{131.7}$ | 300 | 60 | 88 | 3 | 5 | 4 |

TABLE 9

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 49 | $Mo_{12}V_{18}Cu_1Na_{84}O_{124.0}$ | 300 | 62 | 82 | 1 | 7 | 10 |
| 50 | $Mo_{12}V_{18}Cu_{36}Na_{84}O_{159.0}$ | 300 | 78 | 80 | 9 | 6 | 5 |

EXAMPLES 51 AND 52

Catalyst preparation and reaction were carried out in the same manner as in Example 47 except that 2.74 g of sodium hydroxide (Na, 68.6 m-atom) was replaced by each of 2.06 g (Na, 51.5 m-atom) and 3.65 g (Na, 91.5 m-atom) of the sodium hydroxide.

The results are shown in Table 10.

TABLE 10

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 51 | $Mo_{12}V_{18}Cu_{21}Na_{63}O_{133.5}$ | 300 | 73 | 88 | 2 | 7 | 3 |
| 52 | $Mo_{12}V_{18}Cu_{21}Na_{112}O_{158.0}$ | 300 | 71 | 85 | 1 | 9 | 5 |

EXAMPLES 53 TO 60

Catalyst preparation and reaction were carried out in the same manner as in Example 18 except that 1.86 g of sodium hydroxide (Na, 46.6 m-atom) was replaced by each of 2.74 g (Na, 68.6 m-atom) and 3.65 g (Na, 91.5 m-atom) of the sodium hydroxide; 2.88 g (Li, 68.6 m-atom) and 3.84 g (Li, 91.5 m-atom) of the lithium hydroxide; 7.59 g (Mg, 68.6 m-atom) and 23.46 g (Mg, 91.5 m-atom) of the magnesium nitrate; and 18.27 g (Tl, 68.6 m-atom) and 24.37 g (Tl, 91.5 m-atom) of the thallium nitrate.

The results are shown in Table 11.

TABLE 11

| Example | Composition of catalyst | Reaction temperature (°C.) | Conversion of benzoic acid (%) | Selectivity (%) | | | |
|---|---|---|---|---|---|---|---|
| | | | | Phenol | Benzene | Diphenyl + diphenyl ether | Carbon dioxide gas |
| 53 | $Mo_{12}V_{18}Cu_{21}Zn_{1.2}Na_{84}O_{145.2}$ | 300 | 86 | 90 | 1 | 6 | 3 |
| 54 | $Mo_{12}V_{18}Cu_{21}Zn_{1.2}Na_{112}O_{159.2}$ | 300 | 82 | 87 | 1 | 7 | 5 |
| 55 | $Mo_{12}V_{18}Cu_{21}Zn_{1.2}Li_{84}O_{145.2}$ | 300 | 64 | 90 | 0 | 3 | 7 |
| 56 | $Mo_{12}V_{18}Cu_{21}Zn_{1.2}Li_{112}O_{159.2}$ | 300 | 60 | 89 | 0 | 3 | 8 |
| 57 | $Mo_{12}V_{18}Cu_{21}Zn_{1.2}Mg_{84}O_{187.2}$ | 300 | 54 | 90 | 2 | 4 | 1 |
| 58 | $Mo_{12}V_{18}Cu_{21}Zn_{1.2}Mg_{112}O_{201.2}$ | 300 | 49 | 89 | 1 | 5 | 5 |
| 59 | $Mo_{12}V_{18}Cu_{21}Zn_{1.2}Tl_{84}O_{145.2}$ | 300 | 50 | 90 | 1 | 5 | 4 |
| 60 | $Mo_{12}V_{18}Cu_{21}Zn_{1.2}Tl_{112}O_{159.2}$ | 300 | 45 | 88 | 1 | 7 | 4 |

EXAMPLE 61

Reaction was carried out in the same manner as in Example 1 except that benzoic acid was replaced by 4-methylbenzoic acid. As a result, it was found that the conversion of 4-methylbenzoic acid was 45%, and the selectivity of m-cresol, toluene and dimethyldiphenyl+dimethyldiphenyl ether was 81%, 2% and 8%, respectively.

EXAMPLE 62

Reaction was carried out in the same manner as in Example 18 except that benzoic acid was replaced by 4-methylbenzoic acid. As a result, it was found that the conversion of 4-methylbenzoic acid was 80%, and the selectivity of m-cresol, toluene, dimethyldiphenyl+dimethyldiphenyl ether and carbon dioxide gas was 90%, 2%, 5% and 3%, respectively.

What is claimed is:

1. A method for the production of phenol or nucleus-substituted phenols of the formula (II),

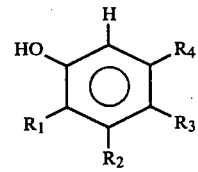

(II)

wherein $R_1$, $R_2$, $R_3$ and $R_4$ are each a hydrogen atom or a methyl group, and/or the formula (III),

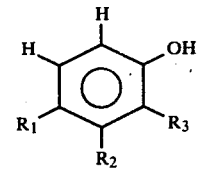

(III)

wherein $R_1$, $R_2$ and $R_3$ are as defined above, comprising the step of catalytically oxidizing benzoic acid or nucleus-substituted benzoic acids of the formula (I),

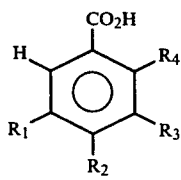

(I)

wherein $R_1$, $R_2$, $R_3$ and $R_4$ are as defined above, in gas phase with an oxygen containing gas at a temperature of 200°–600° C. and with pressures at or above atmospheric, using an oxide catalyst of the formula, $$Mo_aW_bX_cY_dZ_eO_f$$

wherein Mo is molybdenum, W is vanadium, X is at least one of copper, silver, manganese, iron, cobalt, nickel, rhodium, palladium, and platinum, Y is at least one of cerium, uranium, zirconium, chromium, tungsten, zinc, cadmium, tin, phosphorus, antimony, bismuth, and tellurium, Z is at least one of thallium, alkali metals, and alkaline earth metals, and when a is fixed to 12, b is 0.1 to 60, c is 0.1 to 60, d is 0 to 24, e is 0.1 to 120 and f is the number of oxygen atoms satisfying the valence of other elements.

2. A method according to claim 1, wherein the atomic ratio of the components of the catalyst is such that when a is fixed to 12, b is 1 to 24, c is 1 to 40, d is 0 to 12, and e is 12 to 90.

3. A method according to claim 1 using an oxide catalyst of the formula, $$Mo_aW_bX_cY_dZ_eO_f$$

wherein Mo is molybdenum, W is vanadium, X is at least one of copper, silver, palladium and platinum, Y is at least one of zirconium, tungsten, zinc, phosphorus and tellurium, Z is at least one of sodium, lithium, magnesium, and thallium, and when a is fixed to 12, b is 1 to 24, c is 1 to 40, d is 1 to 12, e is 12 to 90 and f is the number of oxygen atoms satisfying the valence of other elements.

4. A method according to claim 1 using an oxide catalyst of the formula, $$Mo_aW_bX_cY_dZ_eO_f$$

wherein Mo is molybdenum, W is vanadium, X is at least one of copper and platinum, Y is at least one of zirconium and zinc, Z is at least one of sodium and lithium, and when a is fixed to 12, b is 1 to 24, c is 1 to 40, d is 1 to 12, e is 12 to 90 and f is the number of oxygen atoms satisfying the valences of other elements.

5. A method according to claims 1, 2, 3 or 4, wherein the oxide catalyst is the one produced by calcining at 500° to 850° C.

6. A method according to claim 1, wherein the gas-phase catalytic oxidation is carried out using steam of 0.5 to 40 times by mole based on benzoic acid or nucleus-substituted benzoic acids.

7. A method according to claim 1, wherein the gas-phase catalytic oxidation is carried out at a space velocity of 100 to 10000 hr$^{-1}$.

* * * * *